United States Patent [19]

Hoffman et al.

[11] Patent Number: 5,055,316
[45] Date of Patent: Oct. 8, 1991

[54] TIGHT BINDING OF PROTEINS TO SURFACES

[75] Inventors: Allan S. Hoffman; Thomas A. Horbett; Janice Bohnert, all of Seattle; Bradford C. Fowler, Bothell; David Kiaei, Seattle, all of Wash.

[73] Assignee: Washington Research Foundation, Seattle, Wash.

[21] Appl. No.: 183,794

[22] Filed: Apr. 20, 1988

[51] Int. Cl.⁵ .............................................. A01N 1/02
[52] U.S. Cl. ........................................ 427/2; 427/40; 427/41; 435/180; 530/402; 530/403; 530/815
[58] Field of Search .............. 427/2, 40, 41; 530/402, 530/403, 815; 435/180

[56] References Cited

U.S. PATENT DOCUMENTS

| 4,720,512 | 1/1988 | Hu et al. | 525/54.1 X |
| 4,743,258 | 5/1988 | Ikada et al. | 427/2 X |
| 4,786,556 | 11/1988 | Hu et al. | 428/447 X |
| 4,836,884 | 6/1989 | McAuslan | 156/629 |
| 4,919,659 | 4/1990 | Horbett et al. | 623/1 |

FOREIGN PATENT DOCUMENTS 83109418.0 4/1984 European Pat. Off. .
84307363.6 5/1985 European Pat. Off. .
86302526.8 10/1986 European Pat. Off. .
PCT/AU86/-00235 2/1987 PCT Int'l Appl. .

OTHER PUBLICATIONS

Joseph et al., Chem. Abstracts 105:12055w.
Sipehia et al., Biomaterials 1986 7:471-473, 1986.
Bohnert et al. (1986) J. Colloid and Interface Science 111: 363-377.
Joseph et al. (1986) J. Biomed. Materials Res. 20:677-682.
Hoffman et al. (1982) Trans. Amer. Soc. Artif. Int. Organs, 18:10-16.
Peters et al. (1973) J. Biol. Chem. 248:2447-2451.
Eberhart et al. (1987) Artificial Organs 11:375-382.
Guidoin et al. (1985) Biomaterials 6:122-128.
Rumisek et al. (1986) J. Vascular Surgery 4:136-143.
Gianazza et al. (1982) Biochem J. 201:129-136.
Cazenave et al. (1987) in Physiochemical and Biochemical Studies, Brash and Horbett (eds.), The American Chemical Society, pp. 537-550.

Primary Examiner—Michael Lusignan
Attorney, Agent, or Firm—Seed and Berry

[57] ABSTRACT

There is disclosed a method for producing extremely tight binding of proteins to surfaces and to a protein surface wherein the protein is tightly bound to the surface.

16 Claims, 7 Drawing Sheets

TIGHT BINDING OF PROTEINS TO SURFACES

TECHNICAL FIELD

This invention relates to methods for producing tight binding of proteins to surfaces, and to a protein surface wherein the protein is tightly bound to the surface.

BACKGROUND ART

The adsorption of proteins, such as albumin or other serum proteins onto surfaces, can create a surface layer that can resist further adsorption of other proteins or cells when placed into contact with an albuminized surface. Thus, an albuminized surface, if the albumin is tightly bound, can create a "biocompatible" coating with bloods or other cellular fluids that contain proteins and/or cells would be ideal for uses such as a vascular graft, cardiovascular implants, catheters, extracorporeal cardiovascular devices (hemodialysis, detoxification, and oxygenation), for titre plates used in clinical diagnostic assays, chromatography separations with protein mixtures, and for detoxifying blood or serum from a chemical that can bind to albumin. Albuminized surfaces do not have widespread use because of the inability to create a tightly bound albumin surface wherein only a relatively insignificant amount of albumin can be removed.

There have been many attempts to treat surfaces with a variety of chemical treatments in order to render the surface more receptive to albumin. The simplest technique is to contact an albumin solution with a surface and incubate it for a specified period of time in the hope that some albumin sticks to the surface. Unfortunately, when the surface is washed, not much albumin remains (Cazenave et al., "Capillary perfusion system for quantitative evaluation of protein absorption and platelet adhesion to artificial surfaces," in *Proteins At Interfaces, Physiochemical and Biochemical Studies, Amer. Chem. Soc.*, pp. 537-550 (1977)). Glutaraldehyde cross-linking of albumin was tried to increase the retention of albumin on the surface, but very little improvement was noted (Guidoin et al., "A Compound Arterial Prosthesis: The Importance of Sterilization Procedure on the Healing and Stability of Albuminated Polyester Grafts," *Biomaterial* 6:122-128 (1985)).

Rumisek et al. ("Heat-Denatured Albumin-Coated Dacron Vascular Grafts: Physical Characteristics And In Vivo Performance," *J. Vascular Surgery* 4:136-143 (1986)) tried steam autoclaving the albuminized surface, in an effort to create a tighter binding through denaturation of the protein. Although there was an improvement, the albuminized surfaces of Rumisek et al. cannot be considered to be "tight binding."

Eberhart et al. ("Albumin Adsorption and Retention on C18-Alkyl-Derivatized Polyurethane Vascular Grafts," *Artificial Organs* 11:375-382 (1987)) refers to a method for grafting carbon alkyl chains to the surface to attempt to increase the surface binding of the albumin. The process of Eberhart et al. is designed to provide for a dynamic exchange of absorbed albumin with albumin in solution. Similarly, Gianazza et al., "A General Method for Fractionation of Plasma Proteins: Dye-Ligand Affinity Chromatography on Immobilized Cibacron Blue 83-6A," *Biochem. J.* 201:129-136 (1982), coupled a dye (Cibacron Blue F3G-A) to hydrophilic supports to allow the dye to complex albumin. Further, Hoffman et al., "Covalent Binding of Biomolecules to Radiation-Grafted Hydrogels on Inert Polymer Surfaces," *Trans. Am. Soc. Int. Organs* 8:10-16 (1982), refers to a method for immobilizing albumin onto hydrogels by cyanogen bromide activation of the hydroxyl groups. Neither of the methods of Eberhardt et al., Gianazza et al. nor Hoffman et al. results in tight binding of albumin to surfaces.

Another method of Joseph et al. ("Platelet Adhesion to Surfaces Treated with Glow Discharge and Albumin," *J. Biomed. Materials Res.* 20:677-682 (1986)) refers to a multistep procedure to increase albumin retention on surfaces. The Joseph et al. method adsorbs albumin onto an untreated surface, exposes the albuminized surface to nitrogen plasma, further adsorbs albumin onto the surface, cross-links the twice albuminized surface with glutaraldehyde and then further adsorbs albumin on the surface for the third time. Despite the rather complicated procedure of Joseph et al., the improvements gained in albumin retention on the surface are small.

Sipehia et al., "Enhanced Albumin Binding to Polypropylene Beads Via Anhydrous Ammonia Gaseous Plasma," *Biomaterials* 7:471-473 (1986), refers to an ammonia gaseous plasma method onto a polypropylene surface to introduce a net positive charge and thereby bind albumin. Since albumin has a net negative charge at physiologic pH, the binding of albumin in Sipehia et al. is presumably through ionic interactions. Although the method of Sipehia et al. does improve albumin binding to the polypropylene surface, it is still not "tight binding" as defined herein.

Accordingly, the ability to tightly bind a serum protein, such as albumin, to a surface to render it biocompatible has been tried with varying procedures. There have been improvements in the ability of albumin to bind to a surface over the simple albumin exposed to a surface method. However, no dramatic improvements resulting in extremely tight binding of albumin or another protein to a surface have been noted.

OBJECTS AND SUMMARY OF THE INVENTION

It is an object of the invention to produce a serum protein-coated surface wherein the serum protein tenaciously binds to the surface such that no more than 25% of the serum protein can be eluted off the surface with detergent washing.

It is a further object of the invention to describe a method to tightly bind a serum protein to a surface using a plasma gas discharge process to pretreat the surface.

The present invention is a method to tightly bind a protein to a surface comprising treating the surface with a plasma gas discharge in the presence of a plasma polymerizable, halogenated hydrocarbon gas and then exposing the plasma gas treated surface to a protein solution, whereby the protein tightly binds to the treated surface. Preferably, the halogenated hydrocarbon gas is a fluorinated hydrocarbon gas of no more than about eight carbon atoms. Preferably, the protein is a serum protein such as an albumin, an immunoglobulin, a fibrinogen, a fibronectin, a Protein-A, or a lipoprotein. Most preferably, the gas is a fluorinated hydrocarbon gas, such as tetrafluoroethylene (TFE), perfluoropropane ($C_3F_8$), or perfluorobutane ($C_4F_{10}$). In a related aspect, the method to tightly bind a protein to a surface comprises treating a fluorocarbon substrate with a RFGD with an etching gas and then adsorbing a protein onto the treated surface. Preferably, the etching gas is argon or helium and the fluorocarbon substrate is polytetrafluoroethylene. In a further related aspect, a substrate can be treated with a predominantly etching halogenated gas, such as $CF_4$, mixed with a plasma polymerizable hydrocarbon gas, such as ethylene, to produce a treated surface. The treated surface is similar to a surface treated with a RFGD of a plasma polymerizable, halogenated hydrocarbon gas.

The invention also comprises a protein-coated surface wherein 25% or less of the protein coated to the surface is elutable with detergent washing. Preferably, the protein coated to the surface is a serum protein such as an albumin, an immunoglobulin, a fibrinogen, or a lipoprotein. The protein-coated surface is made by a method to tightly bind a protein to a surface, comprising treating the surface with a plasma gas discharge in the presence of a plasma polymerizable, halogenated hydrocarbon gas and then exposing the plasma gas-treated surface to a protein solution, whereby the protein tightly binds to the treated surface.

BRIEF DESCRIPTION OF THE DRAWINGS

FIG. 6 is a SDS elutability profile of an untreated PTFE surface and a PET surface treated with RFGD Type III fluorocarbon. There is a dramatic difference in albumin elutability in response to SDS washing. FIG. 6 is an example of the tight binding of albumin characteristic of the present invention.

DETAILED DESCRIPTION OF THE INVENTION

The present invention relates to protein-coated surfaces and to a method for protein coating a surface, wherein the protein is tightly bound to the surface. The protein-coated surface is especially useful as a biocompatible material that can resist further adsorption of other proteins or cells when placed in contact with biological fluids. For example, a biocompatible material, especially a surface coated with albumin, is useful for vascular grafts and for clinical diagnostic plates such as titre plates used for clinical diagnostic tests for AIDS, hepatitis and other diseases. An albuminated surface is resistant to further protein adsorption. The albumin surface is therefore "biocompatible" as an implant or a clinical device. The tightly bound protein layer will reduce nonspecific adsorption of signal-producing protein, resulting in a more efficient separation, thereby reducing the incidence of false positive results in clinical assay procedures. The tightly bound protein on a treated vascular graft will prevent adsorption of other proteins that could initiate the sequence of events that would induce clotting. Further, microelectrodes and biosensor surfaces can be similarly coated so as to avoid nonspecific protein adsorption. Other uses include an albumin or other binding protein surface that can specifically bind a toxin and thereby detoxify a biological fluid.

The protein-coated surface is prepared first by providing an organic surface coating on substrate materials by means of plasma polymerization or RFGD with a halogenated hydrocarbon gas. The surface formed by RFGD is dependent upon the gas present in the chamber. For example, some gases such as argon, are not plasma polymerizable and etch the substrate surface rather than deposit a layer upon the surface. Plasma polymerization gases include halogenated hydrocarbon gases of the present invention such as tetrafluoroethylene, perfluoropropane and other fluorinated hydrocarbons and chlorinated hydrocarbons of no more than eight carbon atoms. Preferably, the plasma polymerizable gas is a fluorinated hydrocarbon having at least as many fluorine atoms as carbon atoms. Most preferably, the plasma polymerizable gas is tetrafluoroethylene.

The treated surface is made by plasma polymerization with a halogenated hydrocarbon gas and deposited by radio frequency glow discharge (RFGD). "Plasma," as used herein, is a "low temperature plasma" or a "cold plasma" produced by RFGD. Plasma created by electric glow discharges contain a variety of species which are chemically active or energetic enough to cause chemical reactions, i.e., covalent bonding to a suitable substrate material. For example, electrons, ions of both charges, excited molecules at various levels of excitation, free radicals, and photons of various energies are created by cold plasma. The treatment of the surface is the deposition of certain halogenated hydrocarbon gases onto clean surfaces of substrate materials for use as tissue implants or other orthopedic implants, blood-contacting devices for diagnosis and/or therapy, microtitre plates for immunoassay, tissue culture plates, catheters, vascular graft material, such as porous, knitted or woven Dacron materials. Deposition refers to the formation of a covalent bond between the substrate and the coating deposited on the substrate surface.

The substrate materials from which the protein-coated surfaces of the present invention are made may include a wide variety of solid materials. Generally, one uses synthetic resins. Synthetic resins include "plastics" such as polyethylene, polyacrylics, polypropylene, polyvinyl chloride, polyamides, polystyrene, polyfluorocarbons and polyesters. Other suitable materials include silicone rubber, hydrocarbon rubbers, polycarbonates and other synthetic resin materials. The substrate may be rigid or flexible, woven or nonwoven, molded or shaped, porous or nonporous. The surfaces of the substrates to be treated are subject to plasma gas discharge in the presence of at least one halogenated hydrocarbon gas to form a treated surface of a homogeneous, tightly bound, mechanically strong, ultra-thin polymer layer on the surface of the substrate. It is believed that the polymer layer on the treated substrate is further characterized as not having a net charge.

In a related aspect, the substrate is polyfluorocarbon and subject to RFGD with an etching-type gas, such as argon, helium and other inert gases. The etched polyfluorocarbon surface is the treated surface that can tightly bind proteins, as described herein. Alternatively, the halogenated hydrocarbon gas can be an etching-type gas, such as $CF_4$ or $C_2F_6$, so long as the etching-type, halogenated hydrocarbon gas is mixed with a plasma polymerizable gas, such as hydrocarbon gas (e.g., ethylene), or a plasma polymerizable, halogenated hydrocarbon gas. The treated surface can still tightly bind proteins.

Preferably, plasma gas polymerization is carried out by positioning the substrate surface in a vacuum chamber, connecting the vacuum chamber to a source of the halogenated hydrocarbon gas, and applying a radio frequency energy to the substrate in the vacuum chamber by means of a suitable generator, along with an impedance matching network. Most preferably, the substrate and RFGD source are moved relative to each other during the application of the high radio frequency energy to allow more uniform coating of plasma. When subjected to the glow discharge energy, the halogenated hydrocarbon gas molecules present in the vapor are bombarded by electrons having high enough energy to rupture carbon-hydrogen bonds (about 4 eV), leading to the formation of free radicals and other chemical species. Suitable halogenated hydrocarbon gases include tetrafluoroethylene, perfluoropropane, and chlorofluoroethylene.

In the treatment of vascular graft materials to render them more biocompatible, particularly more blood compatible, it is preferable to initially clean the vascular graft material prior to exposure to plasma gas discharge, with suitable solvents, followed by drying under vacuum. The graft material surface is then subjected to plasma gas discharge at 1 to 100 watts power in the presence of an atmosphere of inert gas, such as argon, for surface etching and activation of the substrate. Next, a plasma gas discharge treatment at 1 to 100 watts power in the presence of an atmosphere of the halogenated hydrocarbon gas is deposited. The pressures utilized may vary but are generally within 0.10 to 10 torr. The treatment time that the substrate surface is subject to glow discharge may range from about 10 seconds to about 3 hours. The surface coating obtained is uniform over the entire surface of the substrate.

If an immunoglobulin, such as an antibody, is adsorbed onto the treated surface, the immobilized antibody surface is useful for conducting immunoassays. If fibronectin is adsorbed onto the treated surface, the fibronectic coated surface can be used for cell culture or tissue culture applications.

Once the substrate surface is treated, protein is adsorbed onto the substrate surface by exposing the treated surface to a solution containing the particular protein to be adsorbed. Suitable proteins include serum proteins such as albumin, immunoglobulins, fibrinogen, fibronectin, Protein-A, vitronectin, laminin, urokinase, brinolase, and lipoproteins. Preferably, the protein solution is incubated with the treated substrate for approximately two hours at a temperature of approximately 37° C. Albumin can be deposited, for example, by incubation of the treated substrate with an albumin solution or with a blood plasma solution, such as diluted plasma from a baboon. Upon completion of the incubation of the treated substrate with the protein solution, the treated surface is rinsed with an aqueous solution.

Once the protein is adsorbed onto the treated surface, the characteristic of the surface is the tight binding of the protein to the treated surface. Protein binding affinity to the treated surface can be measured by elutability. For example, a protein-treated surface can be washed with a detergent solution such as a solution of one percent SDS (sodium dodecyl sulfate). SDS elutability is measured as the percent of protein eluted from the surface by washing with an aqueous SDS solution. The protein-coated surfaces of the present invention are characterized in that no more than about 25 percent of the protein bound to the treated surface can be eluted from an SDS solution washing of the protein-coated surface. Preferably, no more than 10 percent of the total protein adsorbed onto the treated surface is elutable with an SDS solution washing.

Figure 7:
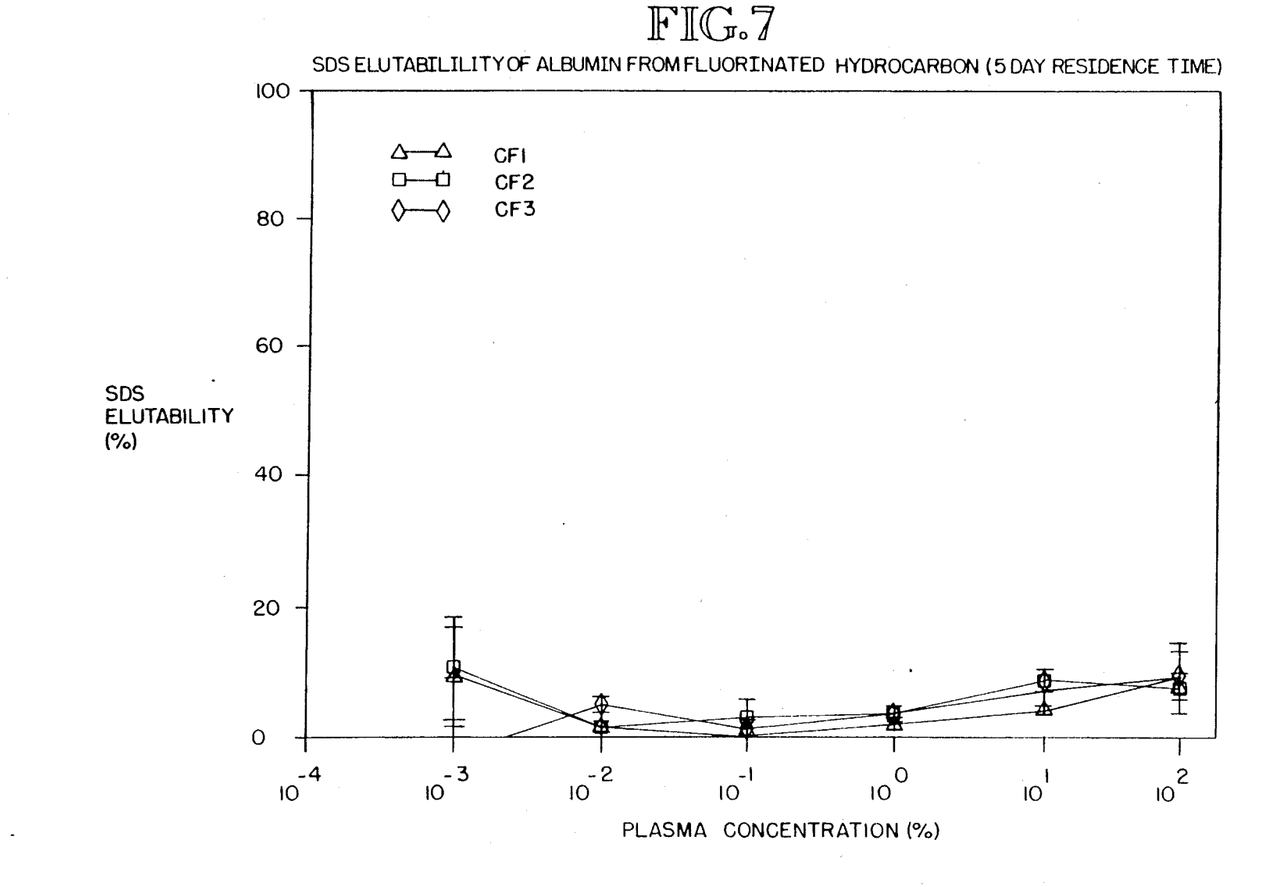
FIG. 7 compares the five-day elutability of albumin from RFGD Type I, Type II and Type III fluorocarbon surfaces as a function of plasma concentration.

The protein-coated surfaces are further characterized by the ability to retain the protein adsorbed onto the surface over an extended period of time. For example, the SDS elutability of the protein albumin adsorbed on a fluorinated hydrocarbon gas-treated surface retains tight binding characteristics over a five-day period. As shown in FIG. 7, the SDS elutabilities of three fluorinated hydrocarbon gas-treated surfaces show very little change in the amount of protein eluting from the surfaces when measured five days after depositing the protein on the surfaces.

The invention is particularly useful for protein coating materials such as vascular grafts that can result in improved healing of vascular implants at the anastomoses and improved endothelialization of the vascular graft. Protein coating of any type of implant can result in improved tissue growth into the implant.

The following examples illustrate the tightness of binding of albumin to a surface of poly(ethylene) terephthalate (PET) or polytetrafluoroethylene (PTFE). The polymer was cleaned and then subjected to radio frequency glow discharge (RFGD), which is the plasma gas treatment. Albumin was used as the protein to be adsorbed onto the treated or untreated surface of the two substrates, PET and PTFE. The substrates were in the form of films and cut into 11 × 16 mm samples, cleaned by ultrasonication in a series of solvents (methylene chloride, acetone, and distilled water), and dried in a vacuum dessicator. The substrates that were treated with a plasma gas discharge were inserted into a tubular (16 mm I.D.) Pyrex reactor in such a way as to allow for exposure of both sides to a glow discharge treatment with the halogenated hydrocarbon gas tetrafluorethylene (Type I and II samples) or perfluoropropane (Type III samples) at selected values of power, pressure, and flow rate. The treated surface was assayed by water contact angle analysis and ESCA as shown in Table 1 below.

TABLE 1

SURFACE CHARACTERISTICS OF MATERIALS

| Material | % of Total Carbon | | | | F/C | Water Contact Angle |
|---|---|---|---|---|---|---|
| | $CF_3$ | $CF_2$ | $CF_1$ | CC | | |
| RFGD-I | 15 ± 1.0 | 21 ± 1.6 | 27 ± 0.8 | 38 ± 2.3 | 1.1 ± 0.08 | 99 ± 1.0 |
| RFGD-II | 19 ± 1.2 | 33 ± 2.0 | 24 ± 2.2 | 24 ± 1.7 | 1.4 ± 0.03 | 98 ± 2.4 |
| RFGD-III | 26 ± 2.5 | 33 ± 1.5 | 21 ± 2.5 | 20 ± 6.1 | 1.5 ± 0.13 | 96 ± 3.2 |
| PTFE | | 100 | | | 1.8 ± 0.37 | 102 ± 2.5 |
| PET | % C = 73 ± 0.4 | | % O = 27 ± 0.3 | | | 72 ± 2.2 |

Surface coverage of the RFGD-treated PET was complete as indicated by the near absence (less than 3 percent) of oxygen. RFGD Type I surface is enriched in $CF_1$ and nonfluorinated carbon groups, RFGD Type II surface is enriched in $CF_2$ groups, and RFGD Type III surface is enriched in both $CF_2$ and $CF_3$ groups.

Albumin was adsorbed with a two-hour, 37° C. incubation of prehydrated samples with diluted baboon plasma solutions containing $^{125}$I-albumin. In a separate experiment, fibrinogen was adsorbed from diluted baboon plasma containing $^{125}$I-fibrinogen. The samples were rinsed, placed in buffer overnight, rinsed again, and the retained radioactivity measured. The amount of protein adsorbed was calculated from the retained radioactivity and the specific activity of the radioisotope. The SDS elutability of adsorbed protein was measured immediately for fibrinogen or after five days after adsorption for albumin. The procedure of SDS elutability was to rinse the protein-coated surfaces and then incubate overnight the protein-coated surface in a 1% aqueous SDS solution. When the protein-coated samples are removed, they are rinsed, and the percent of protein eluted is calculated from the difference in the amount of protein retained by the sample before and after eluting with SDS. The SDS elutability is calculated as percent protein eluted.

EXAMPLE 1

Figure 1:
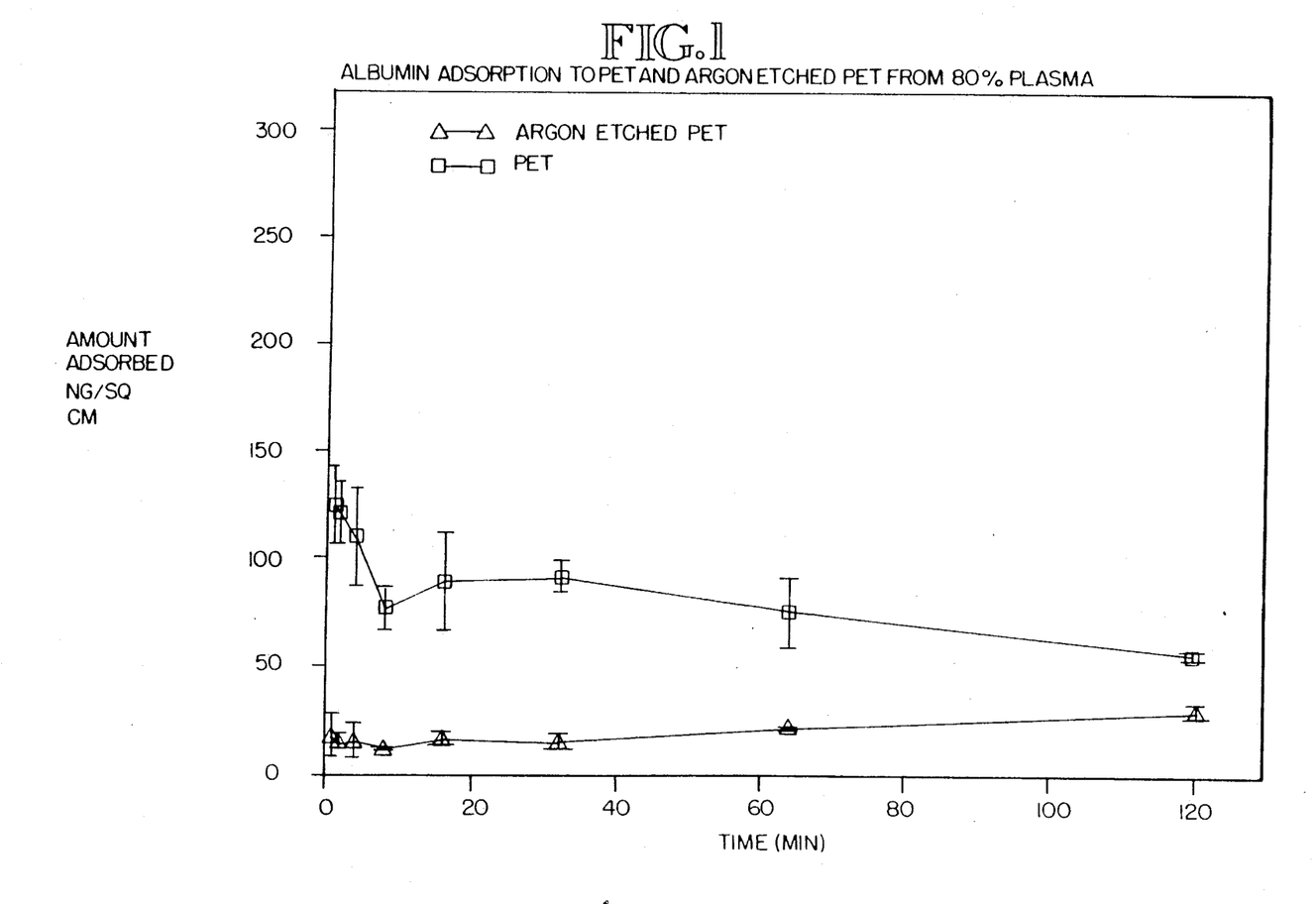
FIG. 1 is a graph showing the amount of adsorbed albumin on a poly(ethylene)terephthalate (PET) surface and on a PET surface etched with a radio frequency glow discharge (RFGD) argon gas. The etching of the surface with argon gas actually reduces the albumin adsorption.
Figure 2:
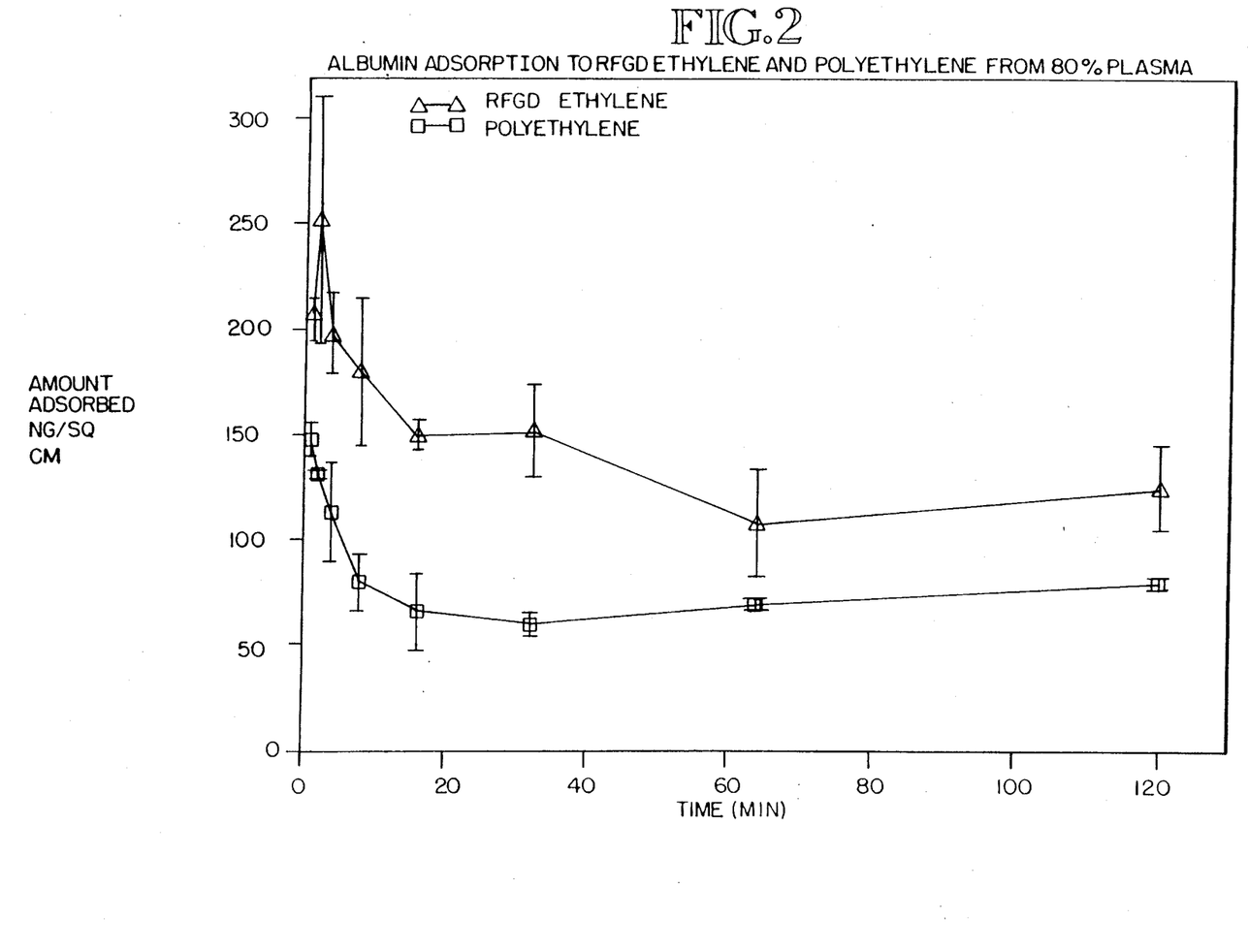
FIG. 2 compares the amount of adsorbed albumin on a polyethylene surface comparing the untreated surface to a RFGD ethylene-treated surface. The RFGD ethylene-treated surface showed higher albumin adsorption.
Figure 3:
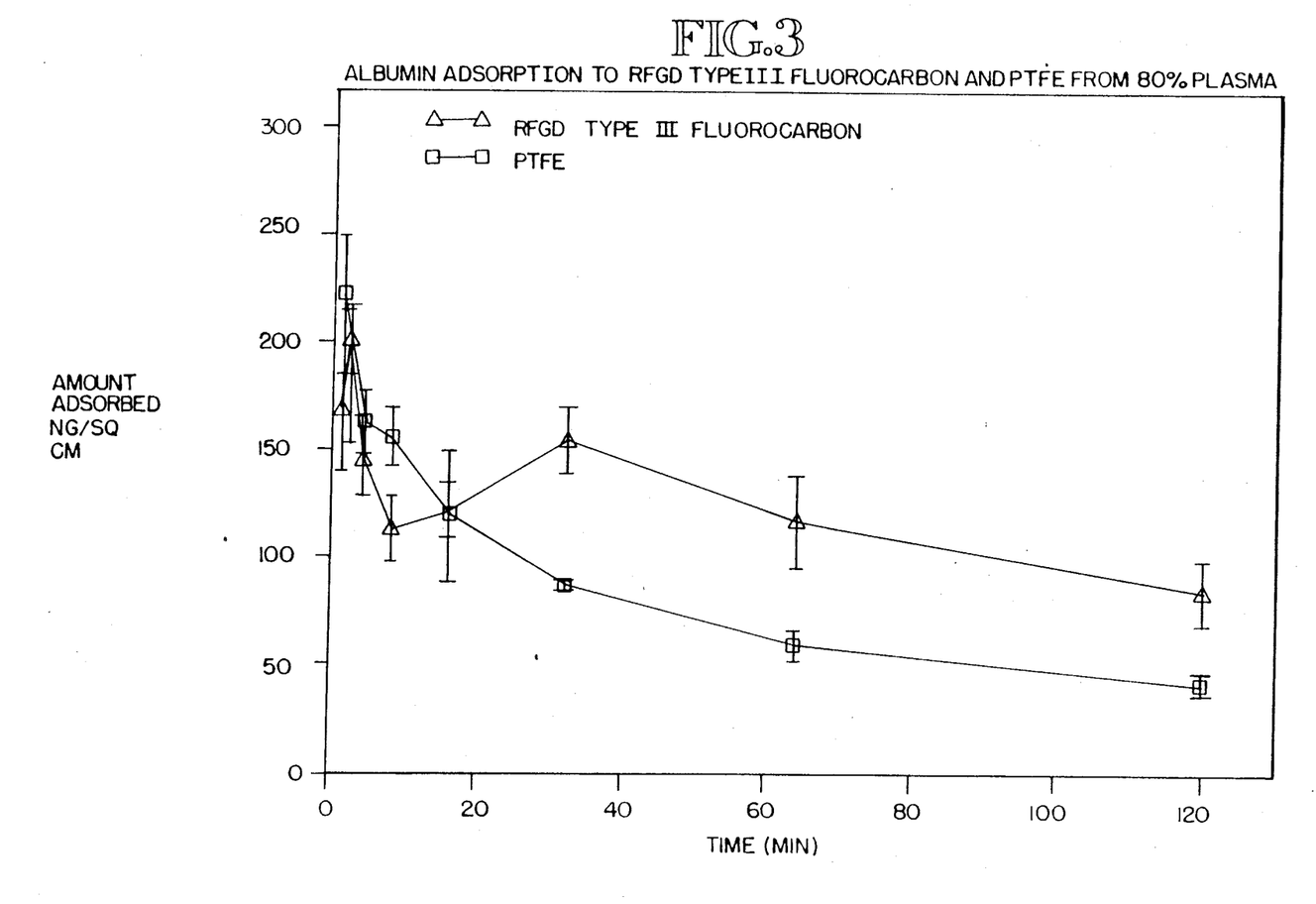
FIG. 3 compares the amount of adsorbed albumin on an untreated polytetrafluoroethylene (PTFE) surface to the PTFE surface treated with RFGD Type II fluorocarbon (e.g., tetrafluoroethylene). Over time, the RFGD Type II fluorocarbon surface exhibited more albumin adsorption.

The kinetics of albumin adsorption to RFGD-treated surfaces and controls from 80% baboon plasma (as the albumin source) at 37° C. are shown in FIGS. 1-3. FIG. 1 shows that the argon-etched PET surface had less albumin adsorbed than the untreated PET surface. FIG. 2 compares an untreated polyethylene surface with a RFGD ethylene (hydrocarbon gas) treated surface. As is seen in FIG. 2, there was more protein adsorption on the RFDG ethylene surface than on the polyethylene untreated surface, but tight binding did not result. In FIGS. 2 and 3, albumin adsorption is higher after 32 minutes to RFGD ethylene and RFGD Type III fluorocarbon as compared to polyethylene and PTFE, whereas albumin adsorption to argon-etched PET is lower than to PET at all adsorption times. The amount of albumin adsorbed to argon-etched PET increases with time, whereas the amount of albumin adsorbed to a surface for the RFGD-deposited hydrocarbon (ethylene) and fluorocarbon decreases with time as do all three control samples. FIGS. 1-3 show that the amount of albumin binding to the RFGD fluorocarbon surface in FIG. 3 is unique to that surface and is not the result of an RFGD plasma treatment, such as an etching treatment with argon on a PET or non-fluorinated polymeric surface or a depositing treatment with the hydrocarbon ethylene.

EXAMPLE 2

Figure 4:
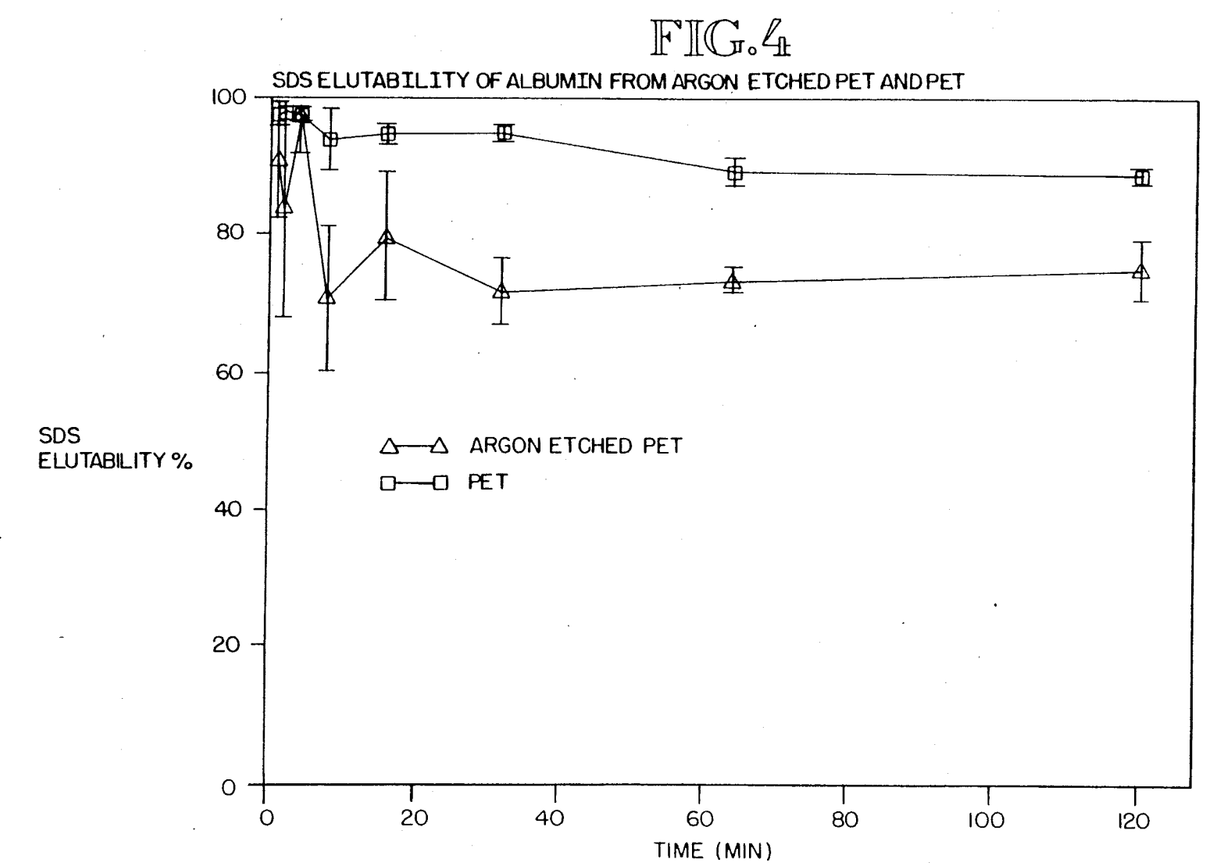
FIG. 4 compares the detergent (sodium dodecyl sulfate or SDS) elutability of albumin from the albumin-adsorbed surfaces of FIG. 1. The SDS elutability profile is expressed as a percentage of the total.
Figure 5:
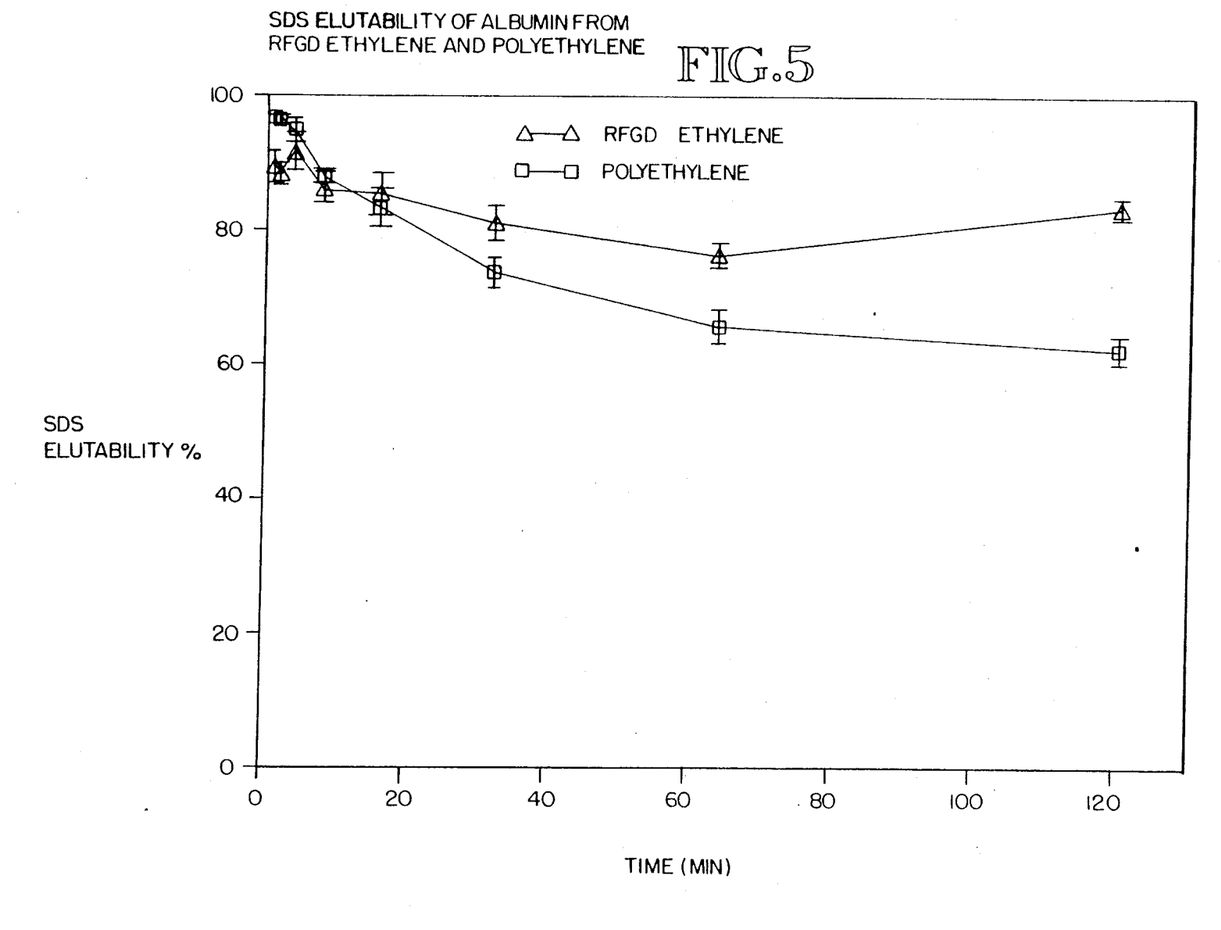
FIG. 5 is a SDS elutability profile of a polyethylene surface and a RFGD ethylene-treated polyethylene surface. Ethylene is a non-halogenated hydrocarbon gas.
Figure 6:
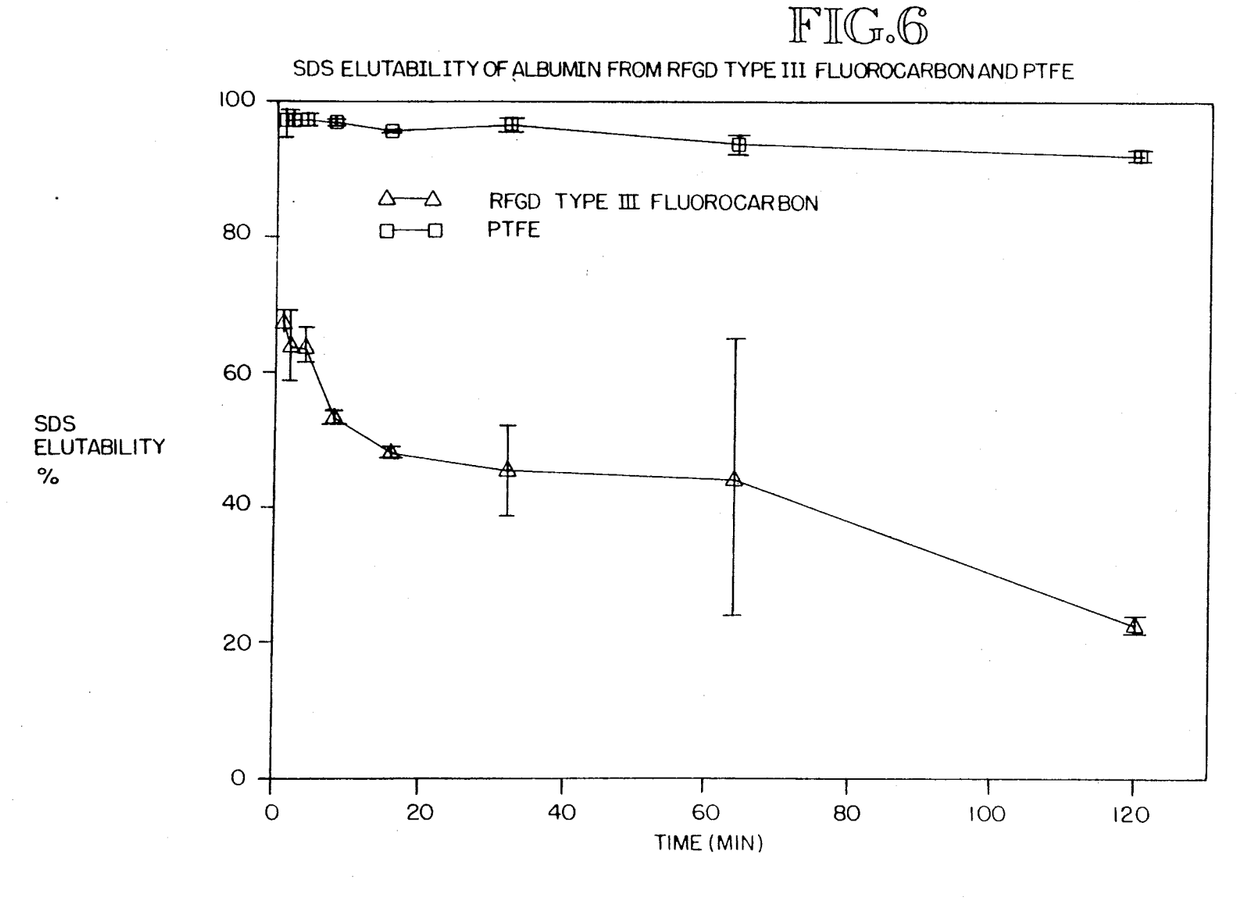

FIGS. 4-6 show the SDS elutability of albumin from RFGD surfaces and control surfaces and the strength of binding of albumin to the surface. The elutability of albumin from RFGD Type III fluorocarbon is significantly less at all adsorption times than that from the other RFGD-treated samples and controls. Albumin elutability drops to 22% after a two-hour adsorption for RFGD Type III fluorocarbon, whereas 60% is the lowest elutability observed among the other five surfaces in FIGS. 4-6. The elutability of albumin drops even lower if the samples are stored in buffer for five days before the albumin is eluted (see FIG. 7). The five-day elutability of albumin was measured in an experiment where albumin was adsorbed from 80% baboon plasma for two hours at 37° C. The five day elutability of albumin from RFGD Type I, II, and III, fluorocarbon was 9%, 7%, and 9%, respectively, whereas elutability from PTFE and PET was only 50%, and 73%, respectively.

Although the foregoing invention has been described, in part, by way of illustration and example for the purposes of clarity and understanding, it will be apparent that certain changes or modifications will be practiced without deviating from the spirit and scope of the invention.

What is claimed is:

1. A method to tightly bind a protein to a surface, comprising:
    treating the surface with a plasma gas discharge in the presence of a plasma polymerizable halogenated hydrocarbon gas to make a plasma gas-treated surface having deposited on the surface a polymerized halogenated hydrocarbon coating; and
    exposing the polymerized halogenated hydrocarbon coating to a protein solution, whereby the protein tightly binds to the coating, and wherein the coating is characterized by not having a net charge.

2. The method of claim 1 wherein the protein is a serum protein.

3. The method of claim 2 wherein the serum protein is selected from the group consisting of albumin, fibrinogen, fibronectin, Protein-A, immunoglobulins, and lipoproteins.

4. The method of claim 3 wherein the serum protein is an albumin.

5. The method of claim 1 wherein the halogenated hydrocarbon gas is plasma polymerizable and contains no more than eight carbon atoms per molecule and at least as many halogen atoms as carbon atoms.

6. The method of claim 5 wherein the halogen atoms of the halogenated hydrocarbon gas are all fluorine atoms.

7. The method of claim 6 wherein the fluorinated hydrocarbon gas is tetrafluoroethylene or perfluoropropane.

8. The method of claim 1 wherein the surface material is selected from the group consisting of polyethylenes, polyacrylics, polypropylene, polyvinyl chloride, polyamides, polystyrenes, polyfluorocarbons, polyesters, silicone rubber, hydrocarbon rubbers, polycarbonates, and other synthetic resin materials.

9. A method to tightly bind a protein to a surface, comprising:

treating the surface with a gas discharge in the presence of a gas mixture of a plasma polymerizable halogenated hydrocarbon gas and an etching inert gas to make a mixed-gas-treated surface having deposited on the surface a polymerized halogenated hydrocarbon coating; and exposing the polymerized halogenated hydrocarbon coating to a protein solution, whereby the protein tightly binds to the coating, and wherein the coating is characterized by not having a net charge.

10. The method of claim 9 wherein the inert gas is selected from the group consisting of $CF_4$, $C_2F_6$, argon, helium, neon, carbon dioxide and nitrogen, and the hydrocarbon gas has no more than eight carbon atoms.

11. The method of claim 9 wherein the protein is a serum protein.

12. The method of claim 11 wherein the serum protein is selected from the group consisting of albumin, fibrinogen, fibronectin, Protein-A, immunoglobulins, and lipoproteins.

13. The method of claim 9 wherein the surface material is selected from the group consisting of polyethylenes, polyacrylics, polypropylene, polyvinyl chloride, polyamides, polystyrenes, polyfluorocarbons, polyesters, silicone rubber, hydrocarbon rubbers, polycarbonates, and other synthetic resin materials.

14. An immunoassay surface wherein an antibody or an antigen is immobilized onto the surface by a method comprising:

treating the surface with a plasma gas discharge in the presence of a plasma polymerizable halogenated hydrocarbon gas to make a plasma gas-treated surface having deposited on the surface a polymerized halogenated hydrocarbon coating; and exposing the polymerized halogenated hydrocarbon coating to an antibody or antigen solution, whereby the antibody or antigen tightly binds to the coating, and wherein the coating is characterized by not having a net charge.

15. A surface treated in accordance with the method of claim 1.

16. A surface treated in accordance with the method of claim 9.

* * * * *

UNITED STATES PATENT AND TRADEMARK OFFICE
CERTIFICATE OF CORRECTION

PATENT NO. : 5,055,316

DATED : October 8, 1991

INVENTOR(S) : Allan S. Hoffman et al

It is certified that error appears in the above-identified patent and that said Letters Patent is hereby corrected as shown below:

On the title page, item [73] Assignee: please change the name of the Assignee from "Washington Research Foundation" to --Board of Regents of the University of Washington--.

Signed and Sealed this

Twenty-third Day of March, 1993

Attest:

STEPHEN G. KUNIN

*Attesting Officer*  *Acting Commissioner of Patents and Trademarks*

UNITED STATES PATENT AND TRADEMARK OFFICE
CERTIFICATE OF CORRECTION

PATENT NO.   :   5,055,316

DATED        :   October 8, 1991

INVENTOR(S)  :   Allan S. Hoffman et al.

It is certified that error appears in the above-identified patent and that said Letters Patent is hereby corrected as shown below:

On title page, item [73] change the name of Assignee from "Washington Research Foundation" to --Board of Regents of the University of Washington --.

In column one, after the heading, "TIGHT BINDING OF PROTEINS TO SURFACES", and before the subtitle, "TECHNICAL FIELD", please insert the following sentence:

--This invention was made with government support under Grant No. HL33229-03 by the National Heart, Lung and Blood Institute, National Institute of Health.--

Signed and Sealed this

Twenty-fourth Day of May, 1994

Attest:

BRUCE LEHMAN

Attesting Officer       Commissioner of Patents and Trademarks